United States Patent [19]

Delprato

[11] Patent Number: 4,762,925
[45] Date of Patent: Aug. 9, 1988

[54] CYAN DYE-FORMING COUPLERS

[75] Inventor: Ivano Delprato, Rocchetta di Cairo Montenotte/Savona, Italy

[73] Assignee: Minnesota Mining and Manufacturing Company, St. Paul, Minn.

[21] Appl. No.: 23,782

[22] Filed: Mar. 9, 1987

Related U.S. Application Data

[62] Division of Ser. No. 856,821, Apr. 28, 1986, Pat. No. 4,672,013, which is a division of Ser. No. 755,266, Jul. 15, 1985, Pat. No. 4,591,548.

[30] Foreign Application Priority Data

Jul. 20, 1984 [IT]  Italy ................ 21992 A/84

[51] Int. Cl.$^4$ .......................................... C07D 265/36
[52] U.S. Cl. .................................................. 544/105
[58] Field of Search ......................................... 544/105

[56] References Cited

U.S. PATENT DOCUMENTS 4,460,581  7/1984  Schromm et al. ............. 544/105 X

FOREIGN PATENT DOCUMENTS 209281  12/1982  Japan .

OTHER PUBLICATIONS

Cox et al, Chemical Abstracts, vol. 82 (1975), 26244a.
Schromm et al, Chemical Abstracts, vol. 93 (1980), 114558p.
Schromm et al, Chemical Abstracts, vol. 99 (1983), 5636r.
Hashimoto et al, Chemical Abstracts, vol. 100 (1984), 138358n.
Vavayannis et al, Chemical Abstracts, vol. 103 (1985), 22229d.
Kobayashi et al, Chemical Abstracts, vol. 105 (1986), 70070h.
Duckworth et al, Chemical Abstracts, vol. 105 (1986), 97484h.
Aoki et al, Chemical Abstracts, vol. 105 (1986), 162145q.

*Primary Examiner*—Richard L. Raymond
*Attorney, Agent, or Firm*—Donald M. Sell; Mark A. Litman

[57] ABSTRACT

Cyan dye-forming 6-hydroxy-2H-1,4-benzoxazin-3-(4H)-one couplers, preferably cyan dye-forming couplers corresponding to the general formula:

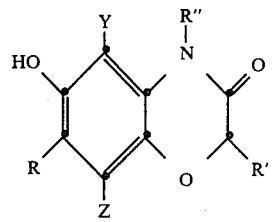

wherein R represents hydrogen or R'''—X—NH, R' represents hydrogen or a substituted or unsubstituted alkyl group, R'' represents hydrogen or R$^{iv}$—X—, X represents a member selected from the group consisting of —CO—, —SO$_2$—, —OCOCO—, —NHCO—, R''' and R$^{iv}$ represent a substituted or unsubstituted alkyl group or a substituted or unsubstituted aryl group and Y and Z, the same or different, represent hydrogen, halogen and a substituted or unsubstituted alkyl or alkoxy group, are described for use in silver halide color photographic processes and elements.

6 Claims, No Drawings

CYAN DYE-FORMING COUPLERS

This is a division of U.S. Ser. No. 856,821 filed Apr. 28, 1986, now U.S. Pat. No. 4,672,013 which is in turn a division of U.S. Ser. No. 755,266 filed July 15, 1985, now U.S. Pat. No. 4,591,548.

FIELD OF THE INVENTION

The present invention relates to 2-equivalent cyan-dye forming 6-hydroxy-2H-1,4-benzoxazin-3-(4H)-one couplers and to silver halide photographic elements and processes employing them.

BACKGROUND OF THE ART

It is known that color photographic images are produced upon development of the light-sensitive silver halides of the photographic elements. A silver image is produced upon reduction of the silver ions with primary aromatic amine type developer compounds in the presence of color couplers which react with the oxidized developer to form a dye in the regions corresponding to the silver image. The substractive three-color photographic process makes use of light-sensitive color photographic elements which include, coated on a support base, one or more red-sensitized silver halide halide emulsion layers, one or more green-sensitized silver halide emulsion layers and one or more blue-sensitized silver halide emulsion layers, wherein cyan, magenta and yellow dye images are respectively formed upon color development of proper couplers.

The couplers normally used to produce cyan image dyes derive from phenols and naphthols (as for instance described in U.S. Pat. Nos. 2,367,351; 2,423,730; 2,474,293; 2,772,161; 2,772,162; 2,895,826; 2,920,961; 3,002,836; 3,476,563; 3,880,661; in FR Pat. Nos. 1,478,188 and 1,497,403 and in GB Pat. No. 2,070,000). Such couplers can be used either in the baths or in the photographic layers. In the latter case, they can bear ballasting substituents, if they are desired not to migrate into the layers and, respectively, hydrophilic or hydrophobic substituents if they are to be introduced into the photographic layer dissolved either in water or in an organic solvent. Upon reaction with the oxidation products of the aromatic primary amino type developing agents, such couplers give indoaniline dyes with consumption of four equivalents of silver ions per mole of dye and preferably two equivalents of silver ions per mole of dye when the reactive methine group (in para position to the phenolic hydroxyl) is substituted by atoms and groups which are splitted off during the coupling reaction (in this latter case the couplers are called 2-equivalent couplers). In the practical use of the cyan-dye forming couplers in the photographic processings, some characteristics of the dyes formed by said couplers after development are thought to be very important in the choise of the couplers, i.e. stability to light, heat and humidity, stability towards the reduction by ferrous ions present in the processings. The loss of density due to an insufficient stability of the dye is the cause of color unbalance in the developed photographic material. Such loss occurs with indoaniline dyes when the bleach and bleach-fixing baths have an insufficiently high redox potential (when, for instance, in the bleach bath containing ferric ions there is a too high concentration of ferrous ions).

To find new classes of dye-forming couplers with characteristics suitable for an optimal use in the photographic materials is desirable even if difficult to be performed.

SUMMARY OF THE INVENTION

According to the present invention there are provided 2-equivalent cyan-dye forming 6-hydroxy-2H-1,4-benzoxazin-3-(4H)-one couplers, preferably 2-equivalent cyan-dye forming couplers corresponding to the following general formula:

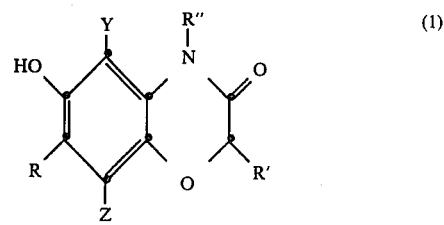

wherein R represents hydrogen or a group R'''—X—NH; R' represents hydrogen or a substituted or unsubstituted alkyl group; R'' represents hydrogen or a group R$^{iv}$—X—; X represents a member selected from the group consisting of —CO—, —SO$_2$—, —OCO-CO— (to form a R'''—O—CO—CO—NH or a R$^{iv}$—O—CO—CO— bond), —NHCO—; R''' and R$^{iv}$ represent a substituted or unsubstituted alkyl group or a substituted or unsubstituted aryl group and Y and Z, the same or different, represent hydrogen, halogen and a substituted or not substituted alkyl or alkoxy group, for use in silver halide color photographic processes and elements.

Such couplers, when associated to the silver halide color photographic materials, upon coupling with the oxidized aromatic primary amine type developing agents, instead of splitting off an atom or a group as usually done by 2-equivalent couplers, open the ether linkage resulting into 2,5-disubstituted cyan iodoaniline dyes very stable to light, heat and humidity, and to bleaching solutions which have a weak oxidation power or are exhausted. The following is the reaction by which the 2-equivalent cyan-dye forming couplers (I) of the invention are converted into cyan indoaniline dyes with the oxidized aromatic primary amine type developing agents, in the presence of silver halide (exposed to light):

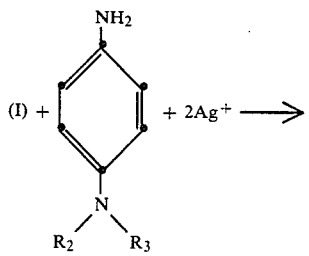

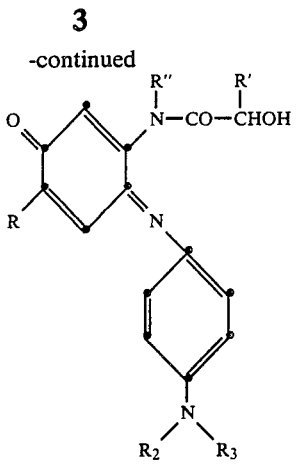

$+ 2Ag^0$ wherein R, R' and R" have the meanings above and $R_2$ and $R_3$ are the substituents of the primary amine type developing agents known in the art.

DETAILED DESCRIPTION OF THE INVENTION

The present invention refers to a process for forming a cyan-dye image in a photographic element comprising a support and a silver halide emulsion, characterized by the step of developing the exposed element with a silver halide color developing agent in the presence of a 2-equivalent cyan dye-forming 6-hydroxy-2H-1,4-benzoxazin-3-(4H)-one coupler.

Preferably the present invention refers to a process as described above, wherein the cyan dye-forming coupler has the general formula (I) already described.

According to another aspect, the present invention relates to 2-equivalent cyan dye-forming couplers having the general formula (I) already described.

Of course in the general formula (I) above, the substituents R, R' and R" are not critical. They can be varied among those known in the art depending upon the desired characteristics of both the couplers and the dyes (deriving therefrom) which are desired (whether water soluble or water immiscible, diffusing or not diffusing, having an absorption shifted towards shorter or longer wavelengths, resistant or not resistant to the formation of the leuco form of the dye in the presence of a weak or partially exhausted bleaching bath). Each of the substituents R, Z, R', R" and Y is to be chosen reasonable in size and nature with reference to what is known in the art to give the desired effects. Particularly, R substituent can be regarded as equivalent to the 2-substituent of a conventional phenolic cyan forming photographic coupler and R" can be regarded as one of the conventional groups normally attached to the 5-position of a phenolic coupler through an amino group. As far as R' substituent is concerned, it is to be chosen in a way as not to make particularly difficult the preparation of the couplers. The expert in the field will be free to introduce in this position any group which he can reasonably think to be useful to get desired characteristics (such as solubility and/or non diffusibility).

In particular, the present invention relates to the cyan dye-forming couplers described above, wherein the group represented by R, R' or R" contains at least 8 carbon atoms.

More in particular, in the general formula (I) above R''' and $R^{iv}$ represents a straight or branched chain alkyl group, or a cyclic alkyl group, preferably an alkyl group having from 1 to 22 carbon atoms (for example a methyl group, an ethyl group, a butyl group, a hexyl group, a tridecyl group, a cyclohexyl group, etc.), an aryl group (for example a phenyl group, a naphthyl group, etc.). These groups can be substituted with one or more substituents selected from an alkyl group (in the case of aryl), a halogen atom, a nitro group, a cyano group, an aryl group (for example a phenyl group, a naphthyl group, etc.), an alkoxy group (for example a methoxy group, an ethoxy group, a methoxyethoxy group, a 2-ethylhexyloxy group, etc.), an aryloxy group (for example a phenoxy group, a 4-hydroxyphenoxy group, a 2,4-ditert.-amylphenoxy group, a naphthoxy group, etc.), a carboxy group, an alkylcarbonyl group (for example an acetyl group, a tetradecanoyl group, etc.), an arylcarbonyl group (for example a benzoyl group, etc.), an alkylcarbonyl group (for example a methoxycarbonyl group, a benzyloxycarbonyl group, etc.), an aryloxycarbonyl group (for example a phenoxycarbonyl group, a p-tolyloxycarbonyl group, etc.), an acyloxy group (for example an acetyloxy group, a tetradecanoyl group, a benzoyl group, etc.), a sulfamoyl group (for example an N-ethylsulfamoyl group, an N-octadecylsulfamoyl group, etc.), a carbamoyl group (for example an N-ethylcarbamoyl group, an N-ethyl-N-dodecylcarbamoyl group, etc.), an acylamino group (for example an acetylamino group, a benzamino group, etc.), a diacylamino group (for example, a succinimido group, a hydantoinyl group, etc.), a ureido group (for example a methylureido group, a phenylureido group, etc.), a sulfonamido group (for example a methansulfonamido group, a dodecansulfonamido group, a methoxyethanesulfonamido group, etc.) and a hydroxy group; X can represent a member selected from the group consisting of —CO—, —SO—, —OCOCO— and —CONH; and R' represents hydrogen or a straight chain or a branched chain or a cyclic alkyl group, preferably an alkyl group having from 1 to 22 carbon atoms (for example a methyl group, an ethyl group, a butyl group, a heptadecyl group, a cyclohexyl group, etc.). These alkyl groups may be substituted with one or more substituents for R described above.

Of course, in the general formula (I) above, the substituents R, R' and R" can be varied among those described above according to particular needs the couplers have to cope with under certain conditions of practical use. In particular, the choise of the R substituent may result important. For instance, to obtain couplers after development giving dyes stable even in partially exhausted bleaching agents, the R substituent shall be preferably an acylamino or ureido group. The wavelength of the absorption maximum of the dye formed by the couplers above can be shifted towards a higher wavelength part of the red portion of the visible spectrum by chosing particular substituents of the acylamino or ureido group, for instance by using partially or totally fluorinated aliphatic chains or benzene rings substituted with electron-attracting groups, such as e.g. halogen, alkoxy, cyan or nitro groups.

Furthermore, in the general formula (I) above, the 5 and 7 positions can be substituted with atoms or groups known in the art; in particular they can be substituted with halogen atoms (e.g. chlorine, bromine and iodine), with alkyl groups (e.g. methyl, trifluoromethyl, ethyl, propyl), with alkoxy groups (e.g. methoxy or ethoxy). Said alkyl and alkoxy groups contain a carbon atom number from 1 to 18, preferably from 1 to 5.

The present invention further relates to a silver halide photographic color element comprising coated on a support at least one light-sensitive silver halide emulsion layer associated with a 2-equivalent cyan-dye forming couplers as described above, in particular a photographic color material comprising coated on a support at least one silver halide emulsion layer, containing in the silver halide emulsion layer or in a non-light-sensitive colloidal layer in water-permeable relationship therewith a 2-equivalent cyan-dye forming photographic coupler as set forth above. Preferably, the silver halide emulsion layer comprising the 2-equivalent cyan-dye forming coupler is a red-sensitized silver halide emulsion layer and the photographic color material further comprises at least one blue-sensitive silver halide emulsion layer and at least one green-sensitive silver halide emulsion layer, said layers being associated with respectively yellow-dye forming and magenta-dye forming couplers.

The present invention also relates to the cyan indoaniline dyes obtained according to the process above (characterized by the reaction of the 2-equivalent cyan-dye forming couplers above with the oxidized aromatic primary amino type color developing agent).

The present invention further relates to an exposed and processed photographic element comprising a support and a layer containing a cyan dye image obtained according to the process above.

Examples of the couplers included in the scope of the present invention are set forth below.

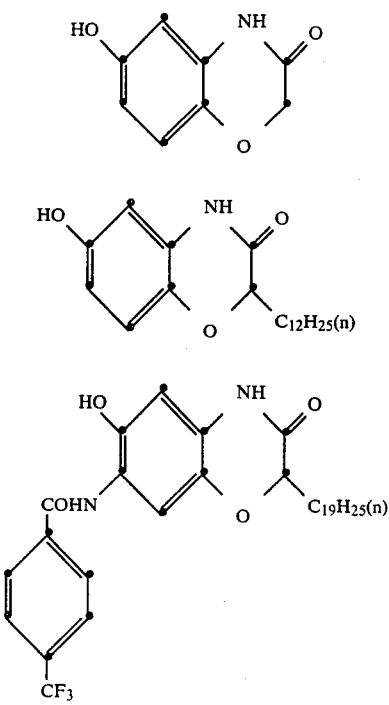

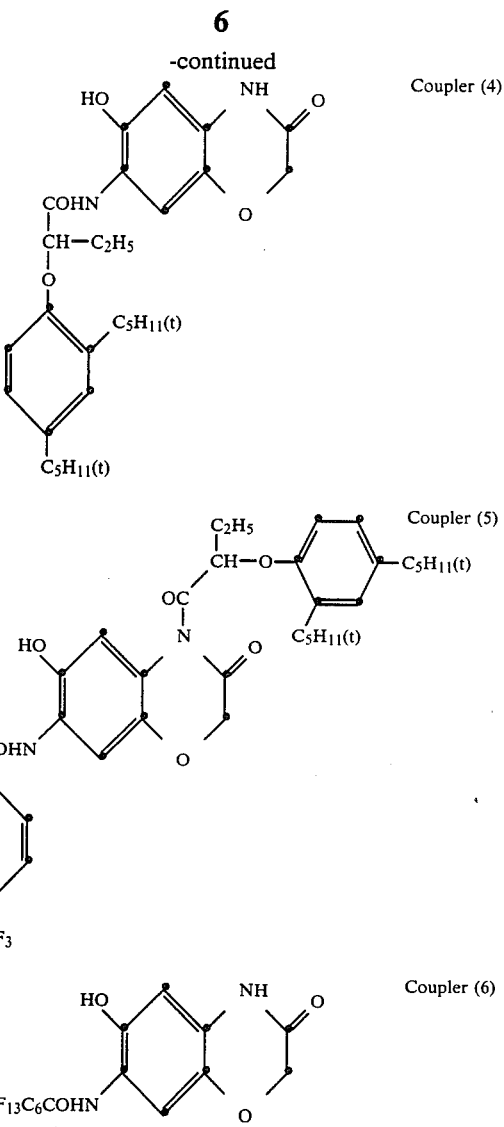

The above compounds can be prepared as described in the illustrative preparations hereinafter.

Preparation 1: Coupler (1)

(a) Acetyloxyanisole 4-hydroxyanisole (210 g, 1.692 mole) and acetic anhydride (690 g, 6.768 mole) were heated at 110° C. for four hours. The solvent was evaporated and the acetylanisole (281 g, 100%) residued as a pale yellow oil. It was used without any further purification.

(b) 2-nitro-4-acetyloxyanisole

Fumic nitric acid ($\delta$1.52, 2.05 ml, 0.05 mole) in chloroform (20 ml) was added dropwise under stirring at 40° C. to the acetyloxyanisole (8.3 g, 0.05 mole) in chloroform (80 ml). The reaction mixture was held at 40° C. for further four hours, then washed with cold water (2×200 ml) and evaporated under vacuum to dryness. The solid residue was crystallized from methanol (20 ml) to give the 2-nitro-4-acetyloxyanisole (3.4 g, 32%) as yellow prisms. The product structure was confirmed by NMR analysis.

(c) 2-nitrohydroquinone

The 2-nitro-4-acetyloxyanisole (160 g, 0.757 mole) in 47% aqueous hydrobromic acid (1,200 ml) was refluxed for 1 hour. The resulting solution was evaporated under vacuum to 200 ml. The 2-nitrohydroquinone (115 g, 78%) separated on cooling as orange prisms.

Percent analysis: Found: C=45.67; H=3.19; N=8.83; $C_6H_5O_4N$ requires C=46.46; H=3.25; N=9.03.

(d) 2-aminohydroquinone

The 2-nitrohydroquinone (24.6 g, 0.159 mole) in THF (250 ml) was reduced under 60 Atm. hydrogen at 60° C. in the presence of Ni Raney catalyst in an autoclave. The resulting amine was not isolated due to easy oxidation by air oxygen.

(e) 2-(α-chloroacetamido)-hydroquinone

α-chloroacetylchloride (10.1 g, 0.128 mole) was added dropwise under stirring at room temperature to the 2-aminohydroquinone (4.16 g, 0.128 mole) in dry acetone (400 ml) and diethanolamine (2.04 ml, 0.128 mole). The reaction mixture was poured into water and hydrochloride acid (2,000 ml, pH 1), then extracted with ethylacetate (500 ml). The solvent was evaporated to dryness and the solid residue (4.20 g, 80%) was used without any further purification. The structure of the 2-(α-chloroacetamido)-hydroquinone was confirmed by NMR analysis.

(f) 6-hydroxy-2H-1,4-benzoxazin-3-(4H)-one (Coupler 1)

30% sodium methoxide in methanol (18.4 g, 0.075 mole) was added under stirring to the 2-(α-chloroacetamido)-hydroquinone (13.4 g, 0.075 mole) in dimethylformamide (DMF 10 ml). The resulting solution was poured into water (150 ml) and the separated solid was Coupler (1) (9 g, 73%).

Percent analysis: Found: C=57.59; H=4.30; N=8.43; $C_8H_7NO_3$ requires C=58.18; H=4.27; N=8.48. The structure was confirmed by NMR analysis.

Preparation 2: Coupler (2)

(a) 2-(α-bromotetradecylamido)-hydroquinone

α-bromotetradecanoic acid (48.8 g, 0.159 mole) and dicyclohexyldicarbodiimide (DCCD, 32.8 g, 0.159 mole) were added to the 2-aminohydroquinone (19.9 g, 0.159 mole) in tetrahydrofurane (THF, 250 ml). After stirring for 1 hour, the reaction mixture was filtered and the liquid evaporated under vacuum. The residue was crystallized from toluene (250 ml) and, on cooling, the 2-(α-bromotetradecanoylamido)-hydroquinone (35 g, 58%) separated as white prisms.

Percent analysis: Found: C=57.30; H=7.76; N=3.36; Br=18.73; $C_{20}H_{32}NBrO$ requires C=57.97; H=7.78; N=3.38; Br=19.23). The formula was confirmed by NMR analysis.

(b) 2-dodecyl-6-hydroxy-2H-1,4-benzoxazin-3-(4H)-one (Coupler 2)

30% sodium methoxide in methanol (15.2 g, 0.084 mole) was added under stirring to 2-(α-bromotetradecylamido)-hydroquinone (35 g, 0.084 mole) in DMF (100 ml). After stirring for 1 hour, the resulting solution was poured into water and the separated solid was crystallized from toluene (200 ml) to give Coupler (2) (15 g, 53%) as white prisms.

Percent analysis: Found: C=71.24; H=9.32; N=4.14; $C_{20}H_{31}NO_3$ requires C=72.03; H=9.37; N=4.20. The formula was confirmed by NMR analysis.

Preparation 3: Coupler (3)

(a) 2-n-dodecyl-6-hydroxy-7-nitro-2H-1,4-benzoxazin-3-(4H)-one

Fumic nitric acid (δ 1.52, 1.4 ml, 0.0336 mole) in acetic acid (16 ml) was added dropwise under stirring at 15° C. to 2-n-dodecyl-6-hydroxy-2H-1,4-benzoxazin-3-(4H)-one (11.2 g, 0.0336 mole) in acetic acid. The 2-n-dodecyl-6-hydroxy-2H-1,4-benzoxazin-3-(4H)-one (5.6 g, 44%) separated as orange prisms and was used as such.

Percent analysis: Found: C=63.25; H=7.90; N=3.65; $C_{20}H_{30}N_2O_5$ requires C=63.47; H=7.99; N=3.71. The structure was confirmed by NMR analysis.

(b) 2-dodecyl-7-amino-6-hydroxy-2H-1,4-benzoxazin-3-(4H)-one

The nitrooxazinone above (4.6 g, 0.0132 mole) in DMF (50 ml) was reduced under 60 Atm. of hydrogen at 60° C. in the presence of Ni Raney catalyst in an autoclave. The resulting amine was not isolated.

(c) 2-n-dodecyl-6-hydroxy-7-(4-trifluoromethyl-phenylureido)-2H-1,4-benzoxazin-3-(4H)-one (Coupler 3)

4-trifluoromethylisocyanate (2.5 g, 0.0132 mole) was added under stirring to the amine (4.23 g, 0.0132 mole) in DMF (25 ml) at 25° C. The resulting solution was poured into cold water and the separated solid was crystallized from a mixture of acetonitrile and ethylacetate=1:1 (25 ml) to give Coupler (3) (3.5 g, 50%) as white prisms. The structure was confirmed by NMR analysis.

Preparation 4: Coupler (4)

(a) 6-hydroxy-7-nitro-2H-1,4-benzoxazin-3-(4H)-one

Fumic nitric acid (δ 1.52, 2.6 ml, 0.062 mole) in acetic acid (5 ml) was added dropwise under stirring to 6-hydroxy-2H-1,4-benzoxazin-3-(4H)-one (Coupler (1), 10.3 g, 0.062 mole) in acetic acid (100 ml) at room temperature. The 6-hydroxy-7-nitro-1,4-benzoxazin-3-one (6.7 g, 51%) separated as yellow prisms.

(b) 6-hydroxy-7-amino-2H-1,4-benzoxazin-3-(4H)-one

The 6-hydroxy-7-nitro-2H-1,4-benzoxazin-3-(4H)-one (17.5 g) in DMF (300 ml) was reduced under 60 Atm. hydrogen at 60° C. in the presence of Ni Raney catalyst in an autoclave. The resulting amine was not isolated.

(c) 6-hydroxy-7-[α-(2,4-ditert.-amylphenoxy)-hexylamido]-2H-1,4-benzoxazin-3-(4H)-one (Coupler 4)

The 6-hydroxy-7-amino-2H-1,4-benzoxazin-3-(4H)-one (13.2 g, 0.0733 mole) was added to α-(2,4-ditert.-amylphenoxy)-hexanoylchloride (26.9 g, 0.0733 mole) in dry acetonitrile. The reaction mixture was refluxed for further 2 hours. Coupler (4) (17.6 g, 47%) separated on cooling as white prisms.

Percent analysis: Found: C=70.36; H=8.26; N=5.50; $C_{30}H_{42}N_2O_5$ requires C=70.56; H=8.29; N=5.49.

Preparation 5: Coupler (5)

(a) 2-nitro-4-benzyloxyphenol

Fumic nitric acid (d=1.52, 43.6 g, 0.70 mole) was dropwise added under stirring to 4-benzyloxyphenol (138.0 g, 0.69 mole) in ethylacetate (500 ml) at 0° C. The resulting solution was raised at room temperature and then washed in separatory funnel with sodium hydrogen carbonate in water (saturated solution). The organic layer was separated and evaporated under vacuum and the residual solid was crystallized from methanol (100 ml) to give nitrophenol (Yield of (a): 62.54 g, 36%) as yellow prisms. The product structure was confirmed by NMR and IR spectra.

Percent analysis: Found: C=64.34; H=4.52; N=5.46. $C_{13}H_{11}NO_4$ requires C=63.67; H=4.52; N=5.71.

(b) 2-amino-4-benzyloxyphenol

Sodium dithionite (174.11 g, 10 moles) in water (400 ml) was dropwise added to the nitrophenol ((a), 93.0 g, 0.38 mole) in refluxing ethanol. The resulting solution was refluxed for further 3 hours, then cooled at room temperature and filtered. The obtained solution was concentrated at a final volume of 100 ml; Water (100 ml) was added and the separated amine ((b), 72.0 g, 88%) was recovered as brown powder.

Percent analysis: Found: C=72.40; H=6.05; N=6.47. $C_{13}H_{13}NO_2$ requires C=72.54, H=6.90, N=6.51

(c) 2-α-bromoacetamido-4-benzyloxyphenol

Bromoacetic acid (13.9 g, 0.01 mole) and dicyclohexyldicarbodiimide (DCCD, 20.6 g, 0.01 mole) were added at room temperature under stirring to the amine ((b), 21.5 g, 0.01 mole) in THF (200 ml). After 1 hour the reaction mixture was filtered and the liquid evaporated to dryness under vacuum. The residue was crystallized from acetic acid (50 ml) to give the bromoamide ((c), 17 g, 50%) as white prisms. The product structure was confirmed by NMR analysis.

Percent analysis: Found: C=54.16; H=4.16; N=4.34 $C_{15}H_{14}NBrO_3$ requires C=53.59, H=4.20, N=4.17

(d) 6-benzyloxy-1,4-benzoxazine-3-one

30% sodium methoxide in methanol (9 g, 0.05 mole) was added under stirring to the amide ((c), 17 g, 0.05 mole) in dimethylformamide (DMF, 50 ml). The resulting solution was poured into water and the separated solid was the oxazinone ((d), 12 g, 94%) which was dried and used without any further purification. The product structure was confirmed by NMR analysis.

(e) 7-nitro-6-benzyloxy-1,4-benzoxazine-3-one

Aqueous 65% nitric acid (5.04 g, 0.052 mole) was added under stirring at room temperature to the oxazinone ((d), 12 g, 0.047 mole) in acetic acid (ml 30). After 1 hour, the separated solid was filtered and washed with acetic acid to give the nitroxazinone ((e), 9 g, 64%) as yellow prisms. The product structure was confirmed by NMR analysis.

Percent analysis: Found: C=59.87; H=4.03; N=9.29 $C_{15}H_{12}N_2O_5$ requires C=60.00, H=4.03, N=9.33.

(f) 4-[α-(2,4-ditert.-pentylphenoxy)-butyroyl]-6-benzyloxy-7-nitro-1,4-benzoxazine-3-one 50% oily-dispersed sodium hydride (2 g, 0.0416 mole) and 88% heptane solution of α-(2,4-ditert-pentylphenoxy)-butanoylchloride (16.02 g, 0.0416 mole) in THF (ml 20) were added under stirring at room temperature to the nitro compound ((e), 12.5 g, 0.0416 mole) in THF (ml 60). After refluxing for half an hour, the reaction mixture was poured into cold water and extracted with ethyl acetate (ml 100). The resulting solution was evaporated to dryness and the residue crystallized from n-heptane (ml 200) to give the product ((g), 18 g, 72%) as yellow prisms. The product structure was confirmed by NMR analysis.

Percent analysis: Found: C=70.10; H=6.94; N=4.45 $C_{35}H_{42}N_2O_7$ requires C=69.74; H=7.02; N=4.65

(g) 4-[α-(2,4-ditert.-pentylphenoxy)-butyroyl]-6-hydroxy-7-amino-1,4-benzoxazine-3-one The nitro compound ((f), 8.19 g, 0.0136 mole) in THF (ml 100) was reduced and debenzylated under 25 PSI hydrogen pressure at room temperature in the presence of 10% Pd on charcoal. The resulting amine (g) was not isolated.

(h) 4-[α-(2,4-ditert.-pentylphenoxy)-butyroyl]-6-hydroxy-7-(4-trifluoromethylphenylureido)-1,4-benzoxazine-3-one 4-Trifluoromethylphenylisocyanate (2.55 g, 0.0136 mole) was added to the amine ((g), 6.56 g, 0.0136 mole) in THF (ml 100). After 1 hour stirring, the solution was evaporated to dryness and the residue crystallized from toluene to give the coupler ((h), 6 g, 67%) as white prisms. The product structure was confirmed by NMR analysis.

Percent analysis: Found: C=64.68; H=6.25; N=6.00 $C_{36}H_{42}N_3F_3O_3$ requires C=64.56; H=6.32; N=6.27.

Preparation 6: Coupler (6)

Perfluoroheptanoic acid (18.9 g, 0.052 mole) and DCCD (10.7 g, 0.052 mole) was added under stirring to the 2-dodecyl-7-amino-6-hydroxy-2H-1,4-benzoxazin-3-(4H)-one (9.4 g, 0.052 mole) in THF (200 ml). After 1 hour stirring, the reaction mixture and the mother liquid was evaporated to dryness. The residue was crystallized from ethanol:water=1:1 to give Coupler (6) (10 g, 50%) as white needles. The structure was confirmed by NMR analysis.

According to the present invention color photographic elements are provided comprising at least one layer of a silver halide emulsion associated with a 2-equivalent cyan-dye forming coupler of the present invention.

With the word "associated" it is meant that the silver halide emulsions and the 2-equivalent cyan-dye forming couplers are so arranged in relation to each other that, upon coupling with the oxidized aromatic primary amine type developing agents, very stable cyan iodoaniline dyes are image-wise produced in the photographic layers. Said 2-equivalent cyan-dye forming couplers may be incorporated in a layer of the silver halide emulsion, in a layer adjacent thereto or in the processing solution.

In a preferred from the 2-equivalent cyan-dye forming couplers are incorporated in the silver halide emulsion layer.

Conventional methods can be employed to incorporate the couplers of the present invention into the silver halide emulsion layers. For example, the couplers can be introduced into the photographic layers with the dispersion technique (a description of such a method can be found in U.S. Pat. Nos. 2,322,027; 2,801,170; 2,801,171 and 2,991,177); said method substantially consists first of dissolving the coupler in a substantially water-immiscible organic solvent and then of dispersing the so-obtained solution under the form of extremely small droplets in the hydrophilic colloidal binder. Gelatin is the preferred colloidal binder, but other known colloidal polymeric binders can also be used.

Another introduction method consists of charging the couplers on droplets of suitable polymeric latexes. This method, which is named "loaded latex method", essentially consists of mixing a solution of the coupler in a water-miscible organic solvent with a polymeric latex consisting of water as a continuous phase and of polymeric particles, having a mean diameter ranging from 0.02 to 0.2 microns, as a dispersed phase. A description of such an introduction method can be found for instance in BE Pat. Nos. 853,512 and 869,816; in U.S. Pat. Nos. 4,214,047 and 4,199,363 and in EP Pat. No. 14,921.

Further, couplers having a water-soluble group, such as a carboxyl group, a hydroxy group, a sulfonic group or a sulfonamido group, can be added to the photographic layer according to the Fisher process, i.e. by dissolving them in an alkaline water solution.

If the couplers are supposed to be introduced into the photographic elements according to the dispersion or loaded-latex techniques above, they must be soluble in substantially water-immiscible organic solvents. This means that the molecule must have hydrophobic substituents for instance aliphatic chains. On the other side, they additionally must bear hydrophobic substituents (for instance $SO_3H$ or COOH), if they must be introduced according to the Fisher process. In any case, if they are to be incorporated into the photographic layers, the 2-equivalent cyan-dye forming couplers of the present invention and the dyes deriving therefrom must be non-diffusing. In order to render them non-diffusing, a group having a hydrophobic residue with about 8 to 22 carbon atoms is introduced into the coupler molecule. Such substituent is called "ballasting substituent". The ballasting substituent is linked to the coupler nucleus directly or through an imino, ether, carbonamido, sulfonamido, ureido, ester, imido, carbamoyl, sulfamoyl, etc. bond. Specific examples of ballasting substituents are illustrated in U.S. Pat. No. 4,009,038.

In a specific embodiment, the photographic elements according to the present invention are intended to produce multicolor images. Said elements contain at least three superimposed color-forming layer units coated on a support. Each of the layer units is comprised of at least one silver halide emulsion layer. The emulsion layers of a first layer unit are primarily responsive to the blue region of the spectrum, the emulsion layers of a second of the layer units are primarily responsive to the green region of the spectrum and the emulsion layers of a third of the layer units are primarily responsive to the red region of the spectrum. The layer units can be coated in any conventional order. In a preferred layer arrangement, the red-responsive layer unit is coated nearest the support and is overcoated by the green-responsive layer unit, a yellow filter layer and a blue-responsive layer unit. The layer units are each associated with at least one image-dye forming compound. (By "associated" is meant that the silver halide emulsion and the dye-forming compounds are so arranged in relation to each other that an interaction between them can take place to produce an image-wise correspondence between the silver image formed and the dye image. The associated image-dye forming compounds may be incorporated in the silver halide emulsion layer or less preferably in a layer adjacent thereto or, but still less preferably, in a development or activator bath).

Incorporated dye-forming couplers constitute exemplary preferred image-dye providing compounds. The blue, green and red-responsive layer units preferably contain yellow, magenta and cyan image-dye providing couplers, respectively.

Conventional open-chain ketomethylene type couplers can be employed as yellow-color-forming couplers. Of these couplers, benzoylacetanilide type and pivaloyl acetanilide type compounds are especially effective. Specific examples of yellow-color forming couplers which can be employed are described for examples in U.S. Pat. Nos. 2,875,057; 3,265,506; 3,408,194; 3,551,155; 3,682,322; 3,725,072 and 3,891,445, West German patent application (OLS) Nos. 2,219,917; 2,261,361 and 2,414,006; British Pat. No. 1,425,020, Japanese patent application No. 10,783/76, Japanese patent application (OPI) Nos. 26,133/72; 73,147/73; 102,636/76; 6,341/75; 123,342/75; 130,442/75; 21,827/76; 87,650/75; 82,424/77 and 115,219/77.

Pyrazolone type compounds, indazolone type compounds, cyanoacetyl compounds, etc., can be employed as magenta-color-forming couplers, and particularly preferred couplers are pyrazolone type compounds. Specific examples of magenta-color-forming couplers which can be employed are those described for example in U.S. Pat. Nos. 2,600,788; 2,983,608; 3,062,653; 3,127,269; 3,311,476; 3,419,391; 3,519,429; 3,558,319; 3,582,322; 3,615,506; 3,834,908 and 3,891,445, West German Pat. No. 1,810,464; West German patent application (OLS) No. 2,408,665; 2,417,945; 2,418,959 and 2,424,467, Japanese patent publication No. 6,031/65, Japanese patent application (OPI) Nos. 20,826/76; 58,922/77; 129,538/74; 74,027/74; 159,336/75; 42,121/77; 74,028/74; 60,233/75; 26,541/76 and 55,122/78.

Phenol type compounds, naphthol type compounds, etc., can be employed as cyan-color-forming couplers in addition in the 2-equivalent cyan-dye-forming couplers of this invention. Specific examples of cyan-color-forming couplers which can be employed are those described for examples in U.S. Pat. Nos. 2,369,929; 2,434,272; 2,474,293; 2,521,908; 2,895,826; 3,034,892; 3,311,476; 3,458,315; 3,476,563; 3,583,971; 3,591,383; 3,767,411 and 4,004,929, German patent application (OLS) Nos. 2,414,830 and 2,454,329 and Japanese patent application (OPI) Nos. 59,838/73; 26,034/76; 5,055/73; 146,828/76; 69,624/77 and 90,932/77.

Colored couplers which can be employed include those described for example in U.S. Pat. Nos. 3,476,560; 2,521,908 and 3,034,892, Japanese patent publication Nos. 2,016/69; 22,335/63; 11,304/67 and 32,461/69, Japanese patent application (OPI) Nos. 26,034/76 and 42,121/77 and German patent application (OLS) No. 2,418,959.

DIR couplers which can be employed include those described, for example, in U.S. Pat. Nos. 3,227,554; 3,617,291; 3,701,783; 3,790,384 and 3,632,345, German patent application (OLS) Nos. 2,414,006; 2,454,301 and 2,454,329, British Pat. No. 953,454, Japanese patent application (OPI) Nos. 69,624/77; 122,335/74 and Japanese patent publication No. 16,141/76.

In addition to DIR couplers, other compounds which release development inhibitors upon development can also be present in the light-sensitive material. For example such DIR compounds as are described in U.S. Pat. Nos. 3,297,445 and 3,379,529, German patent application (OLS) No. 2,417,914, Japanese patent application (OPI) Nos. 15,271/77 and 9,116/78, etc., can be employed.

Two or more kinds of the couplers described above can be incorporated in the same layer, or the same coupler compound can also be present in two or more layers.

Said couplers are made non-diffusing by means of ballasting groups as described above and included into the silver halide emulsion layers of the photographic element by various methods described above.

The present invention is not limited to photographic elements with a particular type of emulsion or of silver halide; it can therefore find an application with photographic elements containing different types of emulsions or of silver halides, such as for instance those described in Research Disclosure 17643, I, December 1978.

The emulsions which can be used in the present invention can be chemically and optically sensitized as described in Research Disclosure 17643, III and IV, December 1978; they can contain optical brighteners, antifogging agents and stabilizers, filtering and antihalo dyes, hardeners, coating aids, plasticizers and lubricants and other auxiliary substances, as for instance described in Research Disclosure 17643, V, VI, VIII, X, XI and XII, December 1978.

The layers of the photographic emulsion and the layers of the photographic element can contain various colloids, alone or in combination, such as binding materials, as for instance described in Research Disclosure 17643, IX, December 1978.

The photographic elements which can be used in the present invention can contain orthochromatic or panchromatic emulsions, as well as unsensitized emulsions. In particular and more preferably, they can be emulsions for color photography containing color-forming couplers, as described in Research Disclosure 17643, VII, December 1978. Such photographic elements, in particular, can be of the negative color print type, or of the reversal type, of the color paper type or of the "movie" positive type. Of course, unconventional photographic materials of the "transfer" type, which make use of negative or direct positive emulsions, such as for instance those described in U.S. Pat. Nos. 3,227,550 and 3,227,551, can use the couplers of the present invention.

The above described emulsions can be coated onto several support bases (cellulose triacetate, paper, resin-coated paper, polyester, included) by adopting various methods, as described in Research Disclosure 17643, XV and XVII, December 1978.

For the production of color photographic images according to the present invention, the silver halide emulsion layers exposed to light radiations to form a latent image, are developed with a compound of the primary aromatic amine type in the presence of the color couplers. Suitable developing compounds are in particular the p-phenylene diamine derivatives, for instance 2-amino-5-diethylamino-toluene chlorohydrate (called CD2), 4-amino-N-ethyl-N-($\beta$-methanesulfonamidoethyl)-m-toluidine sesquisulfate monohydrate (called CD3), 4-amino-3-methyl-N-ethyl-N-($\beta$-hydroxyethyl)-aniline sulfate (called CD4).

After color development, the image-wise developed metallic silver and the remaining silver halide salts generally must be removed from the photographic material. This is preferred in separated bleach and fixing baths, or in a single bath, called blix, which bleaches and fixes in a single processing operation.

The bleaching bath generally is a water solution having a pH equal to 5.60 and containing an oxidizing agent, normally a complex salt of an alkali metal or of ammonium and of trivalent iron with an organic acid, e.g. EDTA.Fe.NH$_4$, where EDTA is the ethylendiaminotetracetic acid. During processing, this bath is continuously aired to oxidize the divalent iron which forms during bleaching the silver image and regenerated, as known in the art, to maintain the bleach effectiveness. The bad working of these operations causes the drawback of the loss of cyan density in the absence of the couplers of the present invention.

Further to the above mentioned oxidizing agent, the blix bath contains known fixing agents, for instance ammonium or alkali metal thiosulfates.

Both bleaching and blix baths can contain other additives, e.g. polyalkylenoxide derivatives, as described in GB Pat. No. 933,008, in order to increase the effectiveness of the bath, or oxythioethers known as bleach accelerators.

In present invention is explained in deeper detail with reference to the examples below, but it should not be construed as being limited thereto.

EXAMPLE 1

A photographic material (Film A) was prepared by coating a cellulose triacetate film base with a light-sensitive layer comprising a mixture respectively of a gelatin silver bromo-iodide (iodide content: 7% mole) and a gelatin silver bromo-chloro-iodide emulsion (chloride content: 5% mole and iodide content: 7% mole) at a silver coverage of 1.3 g/m$^2$, gelatin at a coverage of 2.76 g/m$^2$ and the coupler (3) dispersed in dibutylphthalate and tricresylphosphate, at a coupler coverage of $1.34 \times 10^{-3}$ mole/m$^2$.

Instead of coupler (3), using equimolecular amounts of couplers (4) and (5) according to the present invention, films B and C were respectively prepared in an analogous manner as described above for Film A.

Samples of each film were exposed through a sensitometer wedge and developed for 3' and 36" at 38° C. in a C-41 type developing bath having the following composition:

Na$_2$CO$_3$: 35.00 g
Na$_2$SO$_3$: 4.25 g
KJ: 1.30 g
NaBr: 1.30 g
NH$_2$OH.$\frac{1}{2}$H$_2$SO$_4$: 2.00 g
1,3-diamino-2-propanoltetracetic acid: 2.50 g
4-amino-3-methyl-N-ethyl-N-($\beta$-hydroxyethyl)-aniline sulfate: 4.75 g
Water up to: 1,000 ml
pH at 20° C.: 10.00
then bleach-fixed and washed.

The following results were obtained.

| Film | Coupler | λmax | Fog | Dmax | Speed |
|------|---------|------|------|------|-------|
| A | 3 | 606 | 0.07 | 0.86 | 100 |
| B | 4 | 612 | 0.10 | 0.86 | 132 |
| C | 5 | 654 | 0.12 | 1.18 | 131 |

The above reported results show that, with the introduction of the couplers of the present invention into a silver halide photographic emulsion, after exposure a,d development, good quality images are obtained. The stability to light, heat and humidity of the dyes formed results good as well.

EXAMPLE 2

Four solutions having the following compositions were prepared:

(A) Solution of the couplers:
Coupler: $2 \times 10^{-4}$ moles
Ethyl alcohol to: 100 ml (B) Solution of CD4:
CD4: $2 \times 10^{-4}$ moles
Ethanol*/H$_2$O (90/10 v/v) to: 100 ml

*The mixture ethyl alcohol/H$_2$O has been deaerated by bubbling nitrogen for 1 hour before dissolving CD4 therein.

(C) Solution of the oxidant
Potassium ferricyanide: $10^{-3}$ moles
Water to: 100 ml (D) Buffer solution Sodium acetate: 925 moles Ethyl alcohol/H₂O (90/10 v/v) to 1,000: ml A dye was prepared according to the following method: 1 ml of Solution A) was poured into 30 ml of Buffer Solution D; the resulting mixture was added with 2 ml of Solution B, then with 1 ml of Solution C. After 5 minutes stirring, the wavelength of the maximum absorption (λmax) was measured with a spectrophotometer.

Using couplers (1), (2) and (6) of the present invention, the following results were obtained:

| Coupler | λmax (nm) |
|---------|-----------|
| (1)     | 630       |
| (2)     | 670       |
| (6)     | 674       |

This experiment shows that, using proper substituents in the positions of R and R' in general formula (I), the wavelength of the dye derived from the coupler of the present invention can be varied according to the desired use of the photographic material.

I claim:

1. A 2-equivalent cyan dye-forming coupler having the general formula:

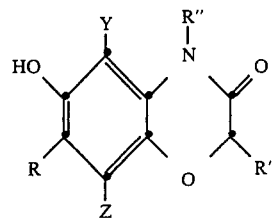

wherein R represents R'''—X—NH, R' represents hydrogen or an alkyl group, R''' represents hydrogen or R$^{iv}$—X—, X represents a member selected from the group consisting of —CO—, —SO—, —OCOC— and —NH—CO—, R''' and R$^{iv}$ represent an alkyl group or an aryl group and Y and Z, the same or different, represent hydrogen, halogen an alkyl or an alkoxy group wherein R''' and R$^{iv}$ may be substituted with groups selected from the group consisting of halogen, nitro, cyano, aryl, alkoxy, aryloxy, carboxy, alkylcarbonyl, aryloxycarbonyl, acyloxy, sulfamoyl, carbamoyl, acylamino, dialkylamino, ureido, sulfonamido and hydroxy.

2. The coupler of claim 1 wherein R is R'''—X—NH and R''' is an alkyl group and X is selected from the group consisting of —CO— and —NHCO—.

3. The coupler of claim 1 wherein R is R'''—X—NH and R''' is an aryl group and X is selected from the group consisting of —CO— and —NHCO—.

4. The coupler of claim 1 wherein at least one of R, R', and R'' contains at least 8 carbon atoms.

5. The coupler of claim 2 wherein at least one of R, R', and R'' contains at least 8 carbon atoms.

6. The coupler of claim 3 wherein at least one of R, R', and R'' contains at least 8 carbon atoms.

* * * * *

UNITED STATES PATENT AND TRADEMARK OFFICE
CERTIFICATE OF CORRECTION

PATENT NO. : 4,762,925

DATED : August 9, 1988

INVENTOR(S) : Delprato

It is certified that error appears in the above-identified patent and that said Letters Patent is hereby corrected as shown below:

Column 10, line 42 "from" should be --form--.

Column 14, line 6 "In" should be --The--.

Claim 1, column 16, line 15 "-SO-" should be -- $-SO_2-$ --.

Signed and Sealed this

Twenty-fourth Day of October, 1989

Attest:

DONALD J. QUIGG

Attesting Officer

Commissioner of Patents and Trademarks